(12) United States Patent
Schupp et al.

(10) Patent No.: US 6,210,935 B1
(45) Date of Patent: Apr. 3, 2001

(54) STAUROSPORIN BIOSYNTHESIS GENE CLUSTERS

(75) Inventors: Thomas Schupp, Möhlin (CH); Nathalie Engel, Kingersheim (FR); Jürg Bietenhader, Liestal (CH); Christiane Toupet, Mulhouse (FR); Andreas Pospiech, Freiburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/029,603

(22) PCT Filed: Aug. 19, 1996

(86) PCT No.: PCT/EP96/03643

§ 371 Date: Mar. 20, 1998

§ 102(e) Date: Mar. 20, 1998

(87) PCT Pub. No.: WO97/08323

PCT Pub. Date: Mar. 6, 1997

(30) Foreign Application Priority Data

Aug. 30, 1995 (EP) .................................................. 95810534

(51) Int. Cl.$^7$ ............................ C12P 12/18; C12N 15/54; C12N 15/61; C12N 15/76; C12N 15/63
(52) U.S. Cl. ................................ 435/119; 435/6; 435/41; 435/252.3; 435/252.35; 435/320.1; 435/471; 536/23.2; 536/24.32; 536/24.33
(58) Field of Search ............................. 435/6, 41, 252.3, 435/252.33, 320.1, 471, 193, 233, 119; 536/24.32, 24.33, 23.2

(56) References Cited

U.S. PATENT DOCUMENTS 4,973,552   11/1990   Schroeder et al. .................... 435/119
5,614,619 *  3/1997   Piepersberg et al. ................ 536/23.2

FOREIGN PATENT DOCUMENTS 0 444 503    9/1991   (EP) .
95/00520     1/1995   (WO) .

OTHER PUBLICATIONS

August P. et al., "Molecular Biological Aspects of Antibiotic Biosynthesis," in *Drug Discovery from Nature*, S. Grabley and R. Thiericke (Eds.), pp. 12.2.2–12.2.3, Springer Publ. (1999).

Cross T. and Goodfellow M., "Taxonomy and Classification of the Actinomycetes," in *Actinomycetales: Characteristics and Practical Importance*, G. Sykes and F.A. Skinner (Eds.), pp. 11–17 (1973).

Malpartida F. et al., Nature, vol. 325 (6107), "Homology between Streptomyces genes coding for synthesis of different polyketides used to clone antibiotic biosynthetic genes", p. 818 (Feb. 26, 1987).

(List continued on next page.)

*Primary Examiner*—Ponnathapu Achutamurthy
*Assistant Examiner*—William W. Moore
(74) *Attorney, Agent, or Firm*—Hesna J. Pfeiffer; Myra H. McCormack; Michael U. Lee

(57) ABSTRACT

The present invention relates especially to a DNA fragment that is obtainable from the gene cluster within the genome of Streptomyces or Actinomyces that is responsible for staurosporin biosynthesis and that contains at least one gene or a part of a gene that codes for a polypeptide that is involved directly or indirectly in the biosynthesis of staurosporin and to methods of preparing said DNA fragment.

Figure 1:
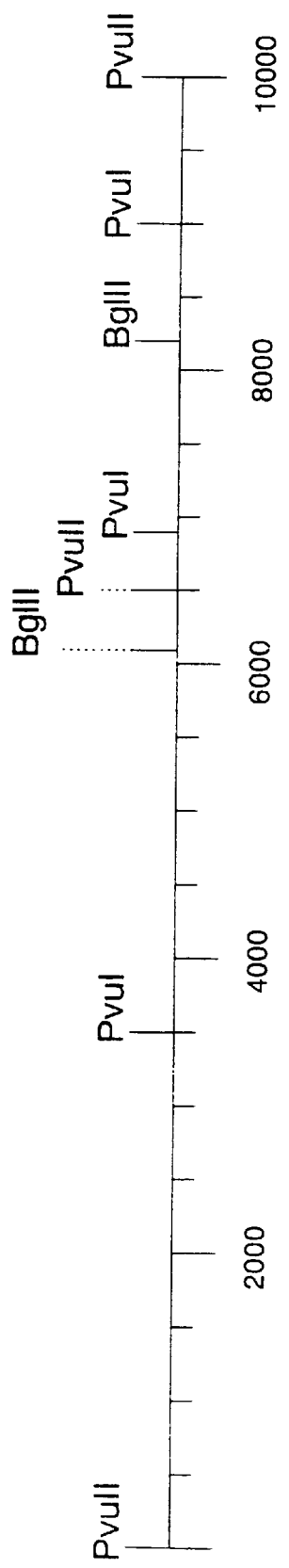

The present invention relates furthermore to recombinant DNA molecules containing one of the DNA fragments according to the invention and to the plasmids and vectors derived therefrom. Also included are host organisms transformed with the said plasmid or vector DNA.

13 Claims, 2 Drawing Sheets

OTHER PUBLICATIONS

Piepersberg W. and Distler J., "10 Aminoglycosides and Sugar Components in Other Secondary Metabolites," in *Biotechnology—vol. 7: Products of Secondary Metabolism*, H–J. Rehm and G. Reed (Eds.), pp. 399, 455–459 (1997).

Schupp T. et al., FEMS Microbiology Letters, vol. 159 "Cloning and sequence analysis of the putative rifamycin polyketide synthase gene cluster from *Amycolatopsis mediterranei*," pp. 201–207 (1998).

Stockmann M. and Piepersberg W., FEMS Microbiology Letters, vol. 69 (2), "Gene probes for the detection of 6–deoxyhexose metabolism in secondary metabolite–producing streptomycetes," (Jan. 1, 1992). Abstract only.

Birnboim & Doly, Nucl. Acids Res. vol. 7, pp. 1513–1523 (1979).

Bush et al., J. Antibiotics, vol. 40, pp. 668–678 (1989).

Cai et al., J.Antibiotics, vol. 48, pp. 143–148 (1995).

Chater, Ciba Found. Symp. vol. 171, pp. 144–162 (1992).

Goeke et al., J. Antibiotics, vol. 48, pp. 428–430 (1995).

Herbert, Natural Product Reports, pp. 185–209 (1991).

Hoehn et al., J. Antibiotics vol. 48, pp. 300–305 (1995).

Hohn & Collins, Gene, vol. 11, p. 291–298 (1980).

Kase et al., J. Antibiotics, vol. 39, pp. 1059–1065 (1980).

Krugel et al., Molecular & General Genetics, vol. 1–2, pp. 193–202 (1993).

Meksuriyen et al., J. Natural Products, vol. 51, pp. 893–899 (1988).

Meyer et al., Int. J. Cancer, vol. 43, pp. 851–856 (1989).

Morioka et al., Agric. Biol. Chem., vol. 49, pp. 1959–1963 (1985).

Nettleton et al., Tetrahedron Lett., vol. 26, pp. 4011–4014 (1985).

Nishizuka, Nature, vol. 308, pp. 693–698 (1984).

Oka et al., Biol. Chem., vol. 50, pp. 2723–2727 (1986).

Omura et al., J. Antibiot., vol. 30, pp. 275–282 (1977).

Pospiech & Neumann, Trends in Genetics, vol. 11, pp. 217–218 (1995).

Reugg & Burgess, Trends in Pharmocological Science, vol. 10, pp. 218–220 (1989).

Schupp et al., FEMS Microbiology Lett., vol. 36, pp. 159–162 (1986).

Schupp et al., FEMS Microbiology Lett., vol. 42, pp. 135–139 (1987).

Smith et al., Methods Enzymol., vol. 151, pp. 461–489 (1987).

Takahashi et al., J. Antibiot., vol. 40, pp. 1782–1783 (1987).

Takahashi et al., J. Antibiot., vol. 42, pp. 571–576 (1989).

Tamaoki et al., Biochem, Biophys. Res. Comm., vol. 135, pp. 397–402 (1986).

Wahl et al., Proc. Natl. Acad. Sci, USA, vol. 84, pp. 2160–2164 (1987).

Ward et al., Mol. Gen. Genet. vol. 203, pp. 468–478 (1986).

Nishizuka, Y., Nature, vol. 334, pp. 661–665 (1988).

* cited by examiner

STAUROSPORIN BIOSYNTHESIS GENE CLUSTERS

This is a 371 of PCT/EP95/03643, filed Aug. 19, 1996.

Staurosporin, an indole-carbazole alkaloid antibiotic, was first isolated from cultures of the microorganism *Streptomyces staurosporens* and described by Omura et al. (Omura et al., J. Antibiot. (1977), 30, 275–282). The biological properties of that secondary metabolite are of exceptional interest and include the following activities:

- inhibitory activity against fungi and yeasts (Omura et al., J. Antibiot. (1977), 30, 275–282),
- strong inhibition of $Ca^{2\circ}$/phospholipid-dependent serine/threonine protein kinases (PKC) (Tamoki et al., Biochem. Biophys. Res. Comm. (1986), 135, 397–402),
- antiproliferative activity (Tamoki et al, Biochem. Biophys. Res. Comm. (1986), 135, 397–402),
- inhibition of platelet aggregation (Oka et al., Biol. Chem. (1986), 50, 2723–2727).

The isoenzyme family of the protein kinase Cs (PKC) plays an important part in signal transduction and cell regulation (Nishizuka, Nature (1988), 334, 661–665). The observation that phorbol esters, which have a tumour-stimulating property, stimulate PKC activity in cells (Nishizuka, Nature (1984), 308, 693–698) led to the conclusion that the inhibition of those enzymes by staurosporin and by similar staurosporin-like compounds could perhaps be used in the chemotherapy of tumours.

Later, staurosporins were isolated from other strains of Streptomyces, for example *Streptomyces longisporoflavus* (strain R-19, DSM 10189), *Streptomyces actuosus* (Morioka et al., Agric. Biol. Chem. (1985), 49, 1959–1963) and Streptomyces species, strain M-193 (Oka et al, Biol. Chem. (1986), 50, 2723–2727) and Streptomyces species, strain 383. Other alkaloids very similar to staurosporin, which contain the same chromophore as staurosporin and exhibit similar biological activity, have also been isolated. Examples are rebeccamycin (Nettleton et al., Tetrahedron Lett. (1985), 26, 4011–4014), UCN-01, UCN02 (Takahashi et al, J. Antibiot. (1987), 40, 1782–1783; Takahashi et al., J. Antibiot. (1989), 42, 571–576) and K-252 (Kase et al., J. Antibiot. (1986), 39,1059–1065), which have also been described as PKC inhibitors or anti-tumour compounds.

Staurosporin has the structure of formula (1)

(1)

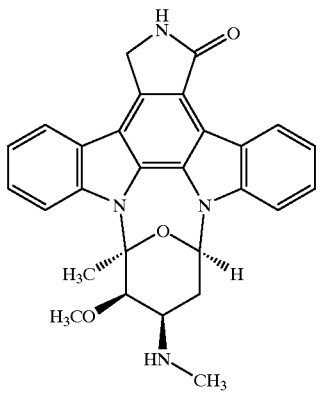

and is an exceptionally strong inhibitor of protein kinase C, but the molecule lacks the selectivity required for pharmaceutical applications involving the very specific inhibition of individual protein kinases. For that reason, analogous compounds based on the fermentation product staurosporin have been prepared by chemical derivatisation at different centres (Ruegg & Burgess, Trends in Pharmacological Science (1989), 10, 218–220). An example thereof is the compound of formula (2) (Meyer et at, Int. J. Cancer (1989), 43, 851–856)

(2)

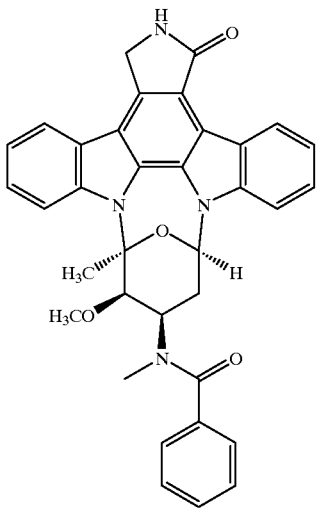

which has selectivity for protein kinase C inhibition and exhibits antiproliferative activity in vitro and anti-tumour properties in vivo.

Streptomyces are gram-positive filamentous bacteria that are found ubiquitously in soil. Streptomyces cultures grow in the form of branching mycelia which, when nutrients are limited, are capable of differentiating further to form aerial mycelia and, finally, to form spores. A special property of that group of microorganisms is their enormous potential for producing an extremely large variety of differently structured metabolites, known as secondary metabolites. Many of those compounds have antibacterial, antifungal, antitumour, immunomodulating or herbicidal properties and are therefore of great practical importance for pharmaceutical or agrochemical use.

Because of the practical importance of microbial secondary metabolites, there is a great deal of interest in understanding the genetic basis of their synthesis in order to create the means to influence them in a targeted manner. That is desirable especially because natural production strains, as in the case of the biosynthesis of staurosporin, generally yield only low concentrations of the secondary metabolites that are of interest. Those concentrations are not sufficient to satisfy the demand for the substance for wide-ranging activity tests and for preclinical and clinical trials, let alone for commercial production.

The genetic basis of secondary metabolite biosynthesis consists essentially in the genes that code for the individual biosynthesis enzymes and in the regulatory elements that control the expression of the biosynthesis genes. In all of the systems investigated hitherto, the secondary metabolite synthesis genes of Streptomyces have been found as clusters of adjacent genes. The size of such antibiotic gene clusters ranges from approximately 10 kilobases (kb) to approaching 100 kb. The clusters normally also contain specific regulator genes and genes for the resistance of the producing organism to its own antibiotic (Chater, Ciba Found. Symp. (1992), 171, 144–162).

In the invention described herein, success has now been achieved, by identifying and cloning genes of staurosporin biosynthesis, in providing the genetic basis for improving in a targeted manner the productivity of staurosporin-synthesising Streptomyces and, especially, of *S. longisporoflavus* or, using genetic methods, for synthesising staurosporin analogues, such as other indole-carbazole alkaloids. In a first step, a staurosporin biosynthesis gene of *S. longisporoflavus* was successfully identified by complementation of a mutant blocked in a biosynthesis step and cloned. Using DNA sequencing, the expected function of the protein derived from the cloned gene in the relevant biosynthesis step of staurosporin was confirmed. On the basis of the DNA sequence, there was found on a cloned 2.1 kb BgIII fragment a second gene that is involved in the synthesis of staurosporin and is likewise capable of complementing a mutant that is blocked in the synthesis of the sugar moiety of the staurosporin molecule. Finally, the cloned DNA fragment was used as a DNA probe for isolating the other staurosporin synthesis genes on large chromosomal DNA fragments of *S. longisporoflavus*.

The gene cluster thus isolated and characterised forms the basis for the targeted optimisation of staurosporin production in *S. longisporoflavus* and other Streptomyces or Actinomyces. The following molecular genetic objectives and/or techniques are of primary importance therein:

- overexpression of individual genes in production strains using plasmid vectors or by the incorporation of additional copies into the chromosome
- study of the expression and transcriptional regulation of the gene cluster during fermentation in different production strains and optimisation thereof by means of physiological parameters and appropriate fermentation conditions
- identification of regulator genes and of the DNA binding sites of the corresponding regulator proteins in the gene cluster. Characterisation of the effect of those regulatory elements on staurosporin production and influencing thereof by means of controlled mutations in those genes or in the DNA binding sites
- duplication of the whole gene cluster or of parts thereof in production strains.

In addition to its use for improving fermentative staurosporin production in accordance with the above description, the gene cluster can likewise be used for the biosynthetic preparation of novel staurosporin analogues. The following possibilities may be mentioned:

- inactivation of individual biosynthesis steps by means of gene disruption
- use of genes of the cluster as DNA probe for isolating from nature Actinomyces or other microorganisms that produce metabolites similar to staurosporin
- replacement of individual elements of the staurosporin gene cluster with those of other indole-carbazole alkaloid-producing Actinomyces, such as rebeccamycin, UCN-01, UCN-02 or K-252, and expression of novel, so-called hybrid metabolites.

DETAILED DESCRIPTION OF THE INVENTION

The present invention relates to an isolated DNA fragment comprising a DNA region that is involved directly or indirectly in the biosynthesis of indole-carbazole alkaloids, including the adjacent DNA regions to the right and left which, because of their function in connection with indole-carbazole alkaloid biosynthesis, qualify as constituents of the indole-carbazole alkaloid gene cluster; and functional fragments thereof.

The present invention relates especially to an isolated DNA fragment comprising a DNA region that is involved directly or indirectly in the biosynthesis of staurosporin, including the adjacent DNA regions to the right and to the left which, because of their function in connection with staurosporin biosynthesis, qualify as constituents of the staurosporin gene cluster.

The DNA fragments according to the invention may contain regulatory sequences, such as promoters, repressor or activator binding sites, repressor or activator genes or terminators; structural genes or information for enzymatic active domains. The invention relates also to any desired combinations of those DNA fragments with one another or with other DNA fragments, such as combinations of promoters, repressor or activator binding sites and/or repressor or activator genes from the indole-carbazole alkaloid gene cluster, especially the staurosporin gene cluster, with foreign structural genes, or combinations of structural genes from the indole-carbazole alkaloid gene cluster, especially the staurosporin gene cluster, with foreign promotors; and combinations of structural genes from different indole-carbazole alkaloid biosynthesis systems. Foreign structural genes code, for example, for proteins that are involved in the biosynthesis of other indole-carbazole alkaloids.

Preference is given to a DNA fragment comprising a DNA region that is involved directly or indirectly in the biosynthesis of staurosporin.

The DNA region or gene cluster described above contains, for example, the genes that code for the individual enzymes that are involved in the biosynthesis of the indole-carbazole alkaloids and especially of staurosporin, and the regulatory elements that control the expression of the biosynthesis genes. The size of such antibiotic gene clusters ranges from approximately 10 kilobases (kb) to approaching 100 kb. The gene clusters normally also contain specific regulator genes and genes for the resistance of the producing organism to its own antibiotic. There are to be understood as enzymes that are involved in the biosynthesis, for example, those that, starting from precursors of tryptophan and glucose, are required for the synthesis of the indole-carbazole alkaloids, such as staurosporin, such as methyl transferases, glucose epimerases, dTDP-glucose synthases (dTDP-glucose pyrophosphorylases), dCDP-glucose synthases (CTP-glucose synthases), hexose-1 -P-nucleotidyl transferases, NDP-glucose 4,6-dehydratases, NDP-4-keto-6-deoxyhexose 3,5-epimerases, secondary metabolitic amino transferases, and enzymes for the conversion of 1-tryptophan (2-molecules) into the indole-carbazole nucleus of staurosporin.

In a further preferred form, the DNA fragment according to the invention is obtained from the gene cluster within the genome of Streptomyces or Actinomyces, and especially of *Streptomyces longisporoflavus,* that is responsible for staurosporin biosynthesis.

Figure 2:
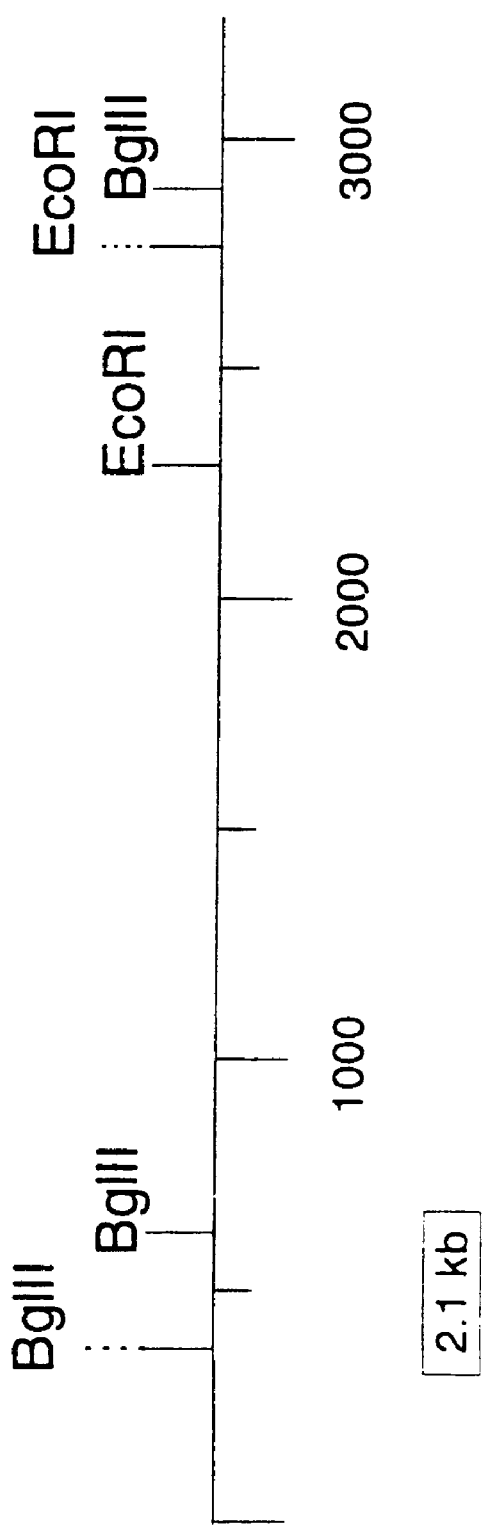

For example, a DNA fragment according to the invention comprises a 35 kb DNA region as shown in FIG. 2, and is preferably a DNA fragment that comprises a 10 kb region as shown in FIG. 1. Special preference is given to a DNA fragment that contains one or more of the partial nucleotide sequences set out in SEQ ID NOs 1, 4 and 5, or functional fragments thereof, and any further DNA sequences in the vicinity of that sequence that, on the basis of homologies present, may be regarded as structural or functional equivalents and are therefore capable of hybridising with that sequence. Examples of other preferred DNA fragments are those that are obtainable in accordance with the method of the invention from the *Streptomyces longisporoflavus* genome and that overlap with the 2.1 kb fragment, such as the following fragments (see also FIG. 1):

EcoRI: >20 kb,
PvuII: 3.5 kb and 6.5 kb;
PvuI: 3.6 kb and 2.1 kb;
BclI: 3.6 kb.

The DNA fragments according to the invention contain, for example, portions of sequence having homologies to the methyl transferases, to amino transferase or to enzymes that are involved in the synthesis of the deoxy sugar moiety of metabolites. In a preferred form, the DNA fragments according to the invention contain portions of sequence having homologies to the methyl transferases and the amino transferases of Streptomyces or Actinomyces, or glucose epimerases, such as dTDP-4-keto-6-deoxyglucose 3,5epimerase; the DNA fragment according to the invention containing in an especially preferred form portions of sequence that code for a methyl transferase. Other especially preferred DNA fragments code for the proteins set out in SEQ ID NO 2 or SEQ ID NO 3, for the proteins represented by the open reading frames in SEQ ID NO 4, or for functional derivatives thereof in each case.

Preference is given also to DNA fragments containing portions of sequence that have homologies to the above-defined 35 kb DNA region or 10 kb DNA region or to SEQ ID NOs 1, 4 and 5 and that can therefore be used as a hybridisation probe within a genomic gene bank of an indole-carbazole alkaloid-producing organism, such as a staurosporin-producing organism, for detecting a constituent of the corresponding gene cluster. The DNA fragment may comprise, for example, exclusively genomic DNA. Special preference is given to a DNA fragment containing the partial nucleotide sequence set out in SEQ ID NO 1, 4 or 5, or a sequence that, on the basis of homologies present, can be regarded as a structural or functional equivalent of the said partial sequence and is therefore capable of hybridising with that sequence.

In order to produce unambiguous signals during hybridisation, the DNA, bonded to filters (e.g. of nylon or nitrocellulose), is usually washed at 55–65° C. in 0.2×SSC (1×SSC=0.15 M sodium chloride, 15 mM sodium citrate).

The expressions 'homologies' and 'structural and/or functional equivalents' refer especially to DNA and amino acid sequences having few or minimal differences between the relevant sequences. Those differences can have very different causes. They may, for example, be mutations or strain-specific differences that occur naturally or are artificially induced or, alternatively, the observable differences with respect to the starting sequence are due to a specific modification that can be introduced, for example, as part of a chemical synthesis.

Functional differences can be regarded as minimal if, for example, the nucleotide sequence coding for a polypetide or a protein sequence has essentially the same characteristic properties as the starting sequence, whether it be in the area of enzymatic activity, immunological reactivity or, in the case of a nucleotide sequence, gene regulation.

Structural differences can be regarded as minimal provided that there is significant overlapping or similarity between the different sequences or that those sequences have at least similar physical properties. The latter include, for example, electrophoretic mobility, chromatographic similarities, sedimentation coefficients, spectrophotometric properties, etc.

In the case of nucleotide sequences, there should be at least 70% identity, preferably 80% and especially 90% or more. In the case of the amino acid sequence, the corresponding values are at least 50%, preferably 60% and especially 70%. An identity of 90% is very especially preferred.

The invention relates also to a hybrid vector containing at least one DNA fragment according to the invention, such as a promotor, a repressor or activator binding site, a repressor or activator gene, a structural gene, a terminator or a functional moiety thereof. The hybrid vector contains, for example, an expression cassette containing a DNA fragment according to the invention that is capable of expressing one or more proteins involved in indole-carbazole alkaloid biosynthesis, and especially in the biosynthesis of staurosporin, or a functional fragment thereof. The invention relates also to a host organism containing the hybrid vector described above.

Suitable vectors that form the starting point for the hybrid vectors according to the invention are generally known, such as pIJ702, pIJ486, pIJ487 and pIJ943.

Suitable host organisms within the scope of the invention are, for example, prokaryotic cells, such as Actinomyces, Pseudomonades, *E. coli,* or eukaryotic cells, such as yeasts and filamentous fungi. Examples of especially suitable host organisms are Streptomyces, such as *Streptomyces staurosporens, Streptomyces longisporoflavus, Streptomyces actuosus,* Streptomyces species, strain M-193 and Streptomyces species, strain 383.

The host organism can be transformed using generally customary methods, for example by means of protoplasting, $Ca^{2+}$, electroporation, viruses, lipid vesicles or a particle gun. The DNA fragments according to the invention may then either be present in the host organism as extrachromosomal constituents or may have been integrated into the chromosome of the host organism via suitable sections of sequence.

The invention relates also to a method of identifying, isolating and cloning a DNA fragment that is obtainable from the gene cluster within the genome of Streptomyces or Actinomyces that is responsible for indole-carbazole alkaloid biosynthesis, especially staurosporin biosynthesis, and that contains at least one gene that is involved directly or indirectly in the biosynthesis of indole-carbazole alkaloids, such as staurosporin, which method comprises the following steps:

a) constructing a representative gene library of an indole-carbazole alkaloid-producing organism, especially a staurosporin-producing organism, from the group of the Streptomyces or Actinomyces, which library contains substantially the entire genome divided into individual clones, b) screening the said clones using a specific DNA probe that hybridises at least with a portion of the gene cluster responsible for the indole-carbazole alkaloid biosynthesis, c) selecting the clones that allow a hybridisation signal with the DNA probe to be recognised; and d) isolating a DNA fragment from the said clone that contains at least one gene that is involved directly or indirectly in the biosynthesis of the indole-carbazole alkaloid.

In a preferred form, the said staurosporin-producing organism is *Streptomyces staurosporens, Streptomyces longisporoflavus, Streptomyces actuosus,* Streptomyces species, strain M-193 or Streptomyces species, strain 383 or, especially, *Streptomyces longisporoflavus.*

The hybridisation probes used are, for example, one of the DNA fragments according to the invention. There may also be used as hybridisation probe sections of sequence originating from the right- and/or left-hand margins of the said DNA fragments.

Special preference is given to a method of identifying and isolating all of the DNA sequences that are involved in the construction of an indole-carbazole alkaloid gene cluster, which method comprises:

a) constructing a representative gene library of an indole-carbazole alkaloid-producing organism from the group of the Streptomyces or Actinomyces, which library contains substantially the entire bacterial genome divided into individual clones;

b) hybridising the said clones, using as probe molecule one of the previously isolated DNA fragments or selected portions thereof that overlap at least with a portion of the adjacent DNA regions to the right and/or left within the gene cluster;

c) selecting the clones that allow a strong hybridisation signal with the DNA probe to be recognised;

d) isolating the fragments containing overlapping DNA regions from the clones selected in accordance with (c) and isolating the fragment that projects furthest beyond the overlapping region;

e) testing the DNA fragment isolated in accordance with (d) for its ability to function within the gene cluster;

f) if it can be demonstrated that the DNA fragment isolated in accordance with (d) functions in the context of the indole-carbazole alkaloid biosynthesis, repeating the method according to steps (a) to (e), the DNA fragment isolated in accordance with (d), or selected portions thereof, especially those from the left- and/or right-hand margin of the said fragment, now acting as the DNA probe, until in the function test for each newly isolated DNA fragment no further functioning is detected in the context of the indolecarbazole alkaloid biosynthesis and the end of the gene cluster has thus been reached; and g) carrying out the method according to steps (a) to (f), if necessary in the other, not hitherto selected, direction.

In order to isolate the DNA fragments according to the invention, the genomic gene banks that synthesise the desired indole-carbazole alkaloid, especially staurosporin, are first produced from the organism strains of interest.

Genomic DNA can be obtained from a host organism in a variety of ways, for example by extraction from the nuclear fraction and purification of the extracted DNA by known methods.

The fragmentation of the genomic DNA to be cloned to a size suitable for insertion into a cloning vector, which fragmentation is required for the production of a representative gene bank, can be effected either by mechanical cutting or, preferably, by cleavage with suitable restriction enzymes. Special preference is given within the scope of this invention to partial cleavage of the genomic DNA, leading to overlapping DNA fragments.

Suitable cloning vectors, which are already used routinely for the production of genomic gene libraries, include, for example, cosmid vectors, plasmid vectors or phage vectors.

Suitable clones containing the desired gene(s) or gene fragment(s) can then be obtained from the gene libraries produced in that manner, using a screening programme.

One possible method of identifying the desired DNA region is, for example, to transform strains that, because of a blocked synthesis path, are not capable of producing staurosporin or other indole-carbazole alkaloids, using the gene bank described above, and to identify those clones which after the transformation are again capable of producing staurosporin (revertants). The vectors that lead to the revertants contain a DNA fragment required in staurosporin synthesis.

A further possible method of identifying the desired DNA region is based, for example, on the use of suitable probe molecules (DNA probe) which are obtained, for example, as described above. Various standard methods are available for identifying suitable clones, such as differential colony hybridisation or plaque hybridisation. When expression gene banks are used, it is possible, moreover, to use immunological detection methods based on the identification of specific translation products.

There may be used as probe molecule, for example, a previously isolated DNA fragment from the same gene or from a structurally related gene that, because of the homologies that are present, is capable of hybridising with the corresponding section of sequence within the desired gene or gene cluster to be identified. Preference is given within the scope of the present invention to the use as probe molecule of a DNA fragment obtainable from a gene or another DNA sequence that plays a role in the synthesis of staurosporin.

If the amino acid sequence of the gene to be isolated, or at least parts of that sequence, are known, it is possible on the basis of that sequence information, in an alternative form of the method, to use an appropriate synthesised DNA sequence for the hybridisations or PCR amplifications.

In order to make the desired gene or parts of a desired gene easier to detect, one of the DNA probe molecules described hereinbefore can be labelled with a suitable readily detectable group. There is to be understood by 'detectable group' within the context of this invention any material that has a specific easily identifiable physical or chemical property.

Special mention may be made at this point of enzymatically active groupings, such as enzymes, enzyme substrates, coenzymes and enzyme inhibitors, also fluorescent and luminescent agents, chromophores and radioisotopes, such as $^3$H, $^{35}$S, $^{32}$P, $^{125}$I and $^{14}$C. The ready detectability of those labels derives on the one hand from their inherent physical properties (e.g. fluorescent labels, chromophores, radioisotopes), and on the other hand from their reaction and binding properties (e.g. enzymes, substrates, coenzymes, inhibitors). Such materials are already widely used, especially in the area of immunoassays, and in the majority of cases can also be used in the present Application.

General methods relating to DNA hybridisation are described, for example, in Maniatis T. et al. (1982).

Those clones within the gene libraries described hereinbefore that are capable of hybridising with a probe molecule and that can be identified using one of the detection methods mentioned above can then be analysed further in order to determine in detail the extent and the nature of the coding sequence.

An alternative method of identifying cloned genes is based on the construction of a gene library made up of plasmid or expression vectors. In that method, analogously to the methods already described hereinbefore, genomic DNA containing the desired gene product is first isolated and then cloned into a suitable plasmid or expression vector. The gene libraries thus produced can then be screened by suitable methods, for example using complementation studies, and the clones that contain the desired gene or at least a portion of that gene as an insert can be selected.

Using the methods described hereinbefore, it is thus possible to isolate a gene that codes for a specific gene product.

For the purpose of further characterisation, the DNA sequences purified and isolated in the manner described hereinbefore are subjected to restriction analysis and to sequence analysis.

For sequence analysis, the previously isolated DNA fragments are first cut into fragments with the aid of suitable restriction enzymes and then cloned into suitable cloning vectors. In order to avoid sequencing errors, it is advantageous to sequence both DNA strands completely.

Various alternative methods are available for analysing the cloned DNA fragment in respect of its function in the context of staurosporin biosynthesis.

For example, it is possible using complementation experiments with defective mutants not only to establish that a gene or gene fragment is in principle involved in the biosynthesis of secondary metabolites, but in addition to verify the specific synthesis step in which the said DNA fragment is involved.

In an alternative form of analysis, the evidence is obtained in exactly the opposite way. By transferring plasmids containing DNA sections having homologies to corresponding sections on the genome, the said homologous DNA sections are integrated via homologous recombination. If, as in the present case, the homologous DNA section is a region within an open reading frame of the gene cluster, the plasmid integration leads to inactivation of the gene as a result of gene disruption and, consequently, to interruption of the production of secondary metabolites. On the basis of current knowledge, it is assumed that a homologous region comprising at least 100 bp, and preferably more than 1000 bp, is sufficient to bring about the desired recombination event.

Preference is given, however, to a homologous region extending over a range of from 0.3 to 4 Kb, especially over a range of from 1 to 3 Kb.

For the production of suitable plasmids having sufficient homology for integration via homologous recombination, a subcloning step is preferably provided in which the previously isolated DNA is digested and fragments of suitable size are isolated and then cloned into a suitable plasmid. Suitable plasmids are, for example, the plasmids generally used for genetic manipulations in Streptomyces, such as pIJ486, pIJ487 and pGMI60.

In principle, it is possible to use any current cloning vectors for the production and replication of the constructs described hereinbefore, for example plasmid or bacteriophage vectors, provided that they have replication and control sequences originating from species compatible with the host cell.

As a rule, a cloning vector carries a replication origin and also specific genes that lead to phenotypic selection features in the transformed host cell, especially resistance to antibiotics. The transformed vectors can be selected on the basis of those phenotypic markers after transformation in a host cell.

Selectable phenotypic markers that can be used within the context of this invention include, for example, without this representing a limitation of the subject of the invention, resistance to thiostreptone, ampicillin, tetracycline, chloramphenicol, hygromycin, G418, kanamycin, neomycin or bleomycin. Prototrophy for specific amino acids can, for example, act as a further selectable marker.

Preference is given within the scope of the present invention especially to Streptomyces and *E. coli* plasmids, such as the plasmids puC18, pUC19 and pIJ486 used in the present invention.

Suitable host cells for the cloning described hereinbefore are, according to this invention, especially prokaryotes, including bacterial hosts, such as Streptomyces, Actinomyces, Pseudomonades or salmonella.

Special preference is given to *E. coli* hosts, such as the *E. coli* strain HB101 or X-1 Blue MR® (Stratagene), or Streptomyces, such as strain TK23.

Competent cells of the *E. coli* strain HB101 are produced by the methods customarily used for the transformation of *E. coli*. For Streptomyces the transformation method according to Hopwood et al (Genetic manipulation of Streptomyces a laboratory manual. The John Innes Foundation, Norwich (1985)) is customarily used.

After transformation and subsequent incubation on a suitable medium, the resulting colonies are subjected to differential screening by plating out onto selective media. The corresponding plasmid DNA can then be isolated from the colonies containing plasmids having cloned-in DNA fragments.

A DNA fragment according to the invention that contains a DNA region involved directly or indirectly in the biosynthesis of staurosporin and that is obtainable in the manner described hereinbefore from the gene cluster of the staurosporin biosynthesis can also be used as a starting clone for the identification and isolation of other, adjacent DNA regions from the said gene cluster that overlap therewith.

That can be achieved, for example, within a gene library consisting of DNA fragments having overlapping DNA regions, by means of 'chromosome walking' using the previously isolated DNA fragment or, especially, its 5' or 3' end sequences. The procedures for chromosome walking are known to a person skilled in the art. Details can be obtained, for example, from the publications of Smith et al. (Methods Enzymol (1987), 151, 461–489) and Wahl et al. (Proc Natl. Acad. Sci, USA (1987), 84, 2160–2164).

A precondition for chromosome walking is the presence within a gene library of clones having DNA fragments that are as long and cohesive as possible and that overlap one another to the greatest possible extent, and of a suitable starting clone that contains a fragment located in the vicinity of or, preferably, inside the region to be analysed. If the precise location of the starting clone is unknown, the walking is preferably carried out in both directions.

The actual walking step begins by using the starting clone, once identified and isolated, as a probe in one of the hybridisation reactions described hereinbefore to trace adjacent clones, which have regions that overlap with the starting clone. By means of hybridisation analysis, the fragment that projects furthest beyond the overlapping region can be determined. That fragment is then used as the starting clone for the second walking step, there being determined in this case the fragment that overlaps with the said second clone in the same direction. In that manner, by means of continuous walking forward along the chromosome, a collection of overlapping DNA clones covering a large DNA region is obtained. Those clones can then be ligated together by known methods, if necessary after carrying out one or more subcloning steps, to form a fragment comprising some or, preferably, all of the components essential for staurosporin biosynthesis.

In the hybridisation reaction for identifying clones having overlapping margins, preference is given to the use of a part fragment from the left- or right-hand margin, which can be obtained by means of a subcloning step, instead of a very large and unwieldy whole fragment. Because of the relatively small size of the said part fragment, fewer positive hybridisation signals are obtained in the hybridisation reaction, with the result that the analysis requires markedly less effort than when the whole fragment is used. It is also advisable for the part fragment to be characterised in detail in order to exclude the possibility that it contains relatively large amounts of repetitive sequences, possibly scattered over the entire genome, which would make a target-specific walking step sequence very much more difficult.

Since the gene cluster responsible for staurosporin biosynthesis covers a relatively large region of the genome, 'large-step walking' or cosmid walking is advantageous according to the present invention. Using cosmid vectors, which allow the cloning of very large DNA fragments, it is possible in those cases to cover a very large DNA region, which may comprise up to 45 Kb, in a single walking step.

In one form of the present invention, for example, for the construction of a cosmid gene bank of Streptomyces or Actinomyces, total DNA of the order of magnitude of DNA fragments of approx. 100 kb is isolated and then partially digested with the aid of suitable restriction endonucleases.

The digested DNA is then extracted in customary manner in order to remove any remaining endonucleases, precipitated and, finally, concentrated. The resulting fragment concentrate is then separated, for example by means of density gradient centrifugation, according to the size of the individual fragments. When the fractions thus obtainable have undergone dialysis, they can be analysed on an agarose gel. The fractions containing fragments of suitable size are pooled and concentrated for further processing. There may be regarded as suitable within the scope of this invention especially fragments of an order of magnitude of from 30 kb to 45 kb, preferably from 40 kb to 45 kb.

In parallel with the fragmentation described above, or later, for example for the subsequent ligase reaction, a suitable cosmid vector, such as pHC79 (Hohn & Collins, Gene (1980), 11, 291) or pWE15® (Stratagene) is completely digested with a suitable restriction enzyme, such as BamHI.

The ligation of the cosmid DNA with the Streptomyces or Actinomyces fragments fractionated according to size can be carried out using a $T_4$-DNA ligase. After an adequate incubation period, the ligation batch so obtainable is packaged into λ-phages by generally known methods.

The resulting phage particles are then used to infect a suitable host strain. Preference is given to a recA⁻ E. coli strain, such as E. coli HB101 or X-1 Blue® (Stratagene). The selection of transfected clones and the isolation of the plasmid DNA can be carried out using generally known methods.

Screening of the gene bank for DNA fragments that play a role in staurosporin biosynthesis is carried out using a specific hybridisation probe which is assumed (for example on the basis of complementation tests or gene disruption) to contain DNA regions of the staurosporin gene cluster.

Differential screening of the resulting transformed colonies can be used to detect suitable colonies and to isolate their plasmid DNA (Maniatis et al., 1982; pp. 368–369). The isolated plasmid DNA is then cleaved with a suitable restriction enzyme and analysed by means of agarose gel electrophoresis for the size of the inserted fragments, the previously selected plasmid PSLO18/10 being used, for example, as reference standard.

A plasmid containing an additional fragment of the desired size can then be isolated from the gel in the manner described hereinbefore. Confirmation that the additional fragment is identical to the desired fragment of the previously selected cosmid can then be obtained by means of Southern transfer and hybridisation.

Analysis of the function of the DNA fragments thus isolated can be carried out within the context of a gene disruption experiment, as described hereinbefore.

The invention relates also to the use of the DNA fragments, hybrid vectors, expression cassettes or transformed host organisms according to the invention in the preparation of indole-carbazole alkaloids and especially of staurosporin and its precursors or derivatives.

Derivatives of staurosporin are customarily understood as being those having modified substitution patterns which either serve as the starting point for further modifications or can themselves be used as active ingredients or prodrugs.

The DNA fragments, hybrid vectors or expression cassettes according to the invention can be used both in the preparation of indole-carbazole alkaloids, and especially staurosporin, in host organisms not previously capable of producing indole-carbazole alkaloids and to improve the yield in organisms already producing indole-carbazole alkaloids. For that purpose, for example, a plurality of copies of relevant DNA fragments can be inserted into the host organisms, or the regulatory mechanisms of indole-carbazole alkaloid biosynthesis, and especially of staurosporin biosynthesis, can be analysed and modified in order to improve production. It is also possible, by combining DNA fragments from indole-carbazole alkaloid gene clusters with other DNA fragments, for example, to replace specific enzymes, in order to produce derivatives of those alkaloids.

A further possible use of the DNA fragments according to the invention consists in inactivating enzymes that are involved in indole-carbazole alkaloid biosynthesis or in using the DNA fragments according to the invention in the synthesis of oligonucleotides which are then used in the context of PCR amplification to detect homologous sequences.

FIGURES

FIG. 1 10 kb DNA region containing a number of important restriction cleavage sites FIG. 2 35 kb DNA region containing a number of important restriction cleavage sites

EXAMPLES

All liquid cultures of S. longisporoflavus are carried out in Erlenmeyer flasks at 28° C. or 30° C. on a shaker at 250 rpm. General molecular genetic techniques, such as agarose gel electrophoresis, restriction digestion, DNA purification by ethanol precipitation, and DNA isolation from agarose, are carried out as described in Maniatis et al., Molecular Cloning: A laboratory manual, 1st Edn. Cold Spring Harbor Laboratory Press, Cold Spring Harbor, N.Y. (1982) or in Sambrook et al., Molecular Cloning: A laboratory manual, 2nd Edn. Cold Spring Harbor Laboratory Press, Cold Spring Harbor, N.Y., 1989.

| | |
|---|---|
| LB | Maniatis et al., Molecular Cloning: A laboratory manual, 1st Edn. Cold Spring Harbor Laboratory Press, Cold Spring Harbor NY (1982) |
| TSB medium | Hopwood et al. (Genetic manipulation of Streptomyces, a laboratory manual. The John Innes Foundation, Norwich (1985)) |
| minimal agar (MM) | Hopwood et al. (Genetic manipulation of Streptomyces, a laboratory manual. The John Innes Foundation, Norwich (1985)) |
| R2YE agar plate | Hopwood et al. (Genetic manipulation of Streptomyces, a laboratory manual. The John Innes Foundation, Norwich (1985)) |

-continued

| | |
|---|---|
| DST (=SNA) soft agar | Hopwood et al. (Genetic manipulation of Streptomyces, a laboratory manual. The John Innes Foundation, Norwich (1985)) |
| NL148 (=NL148G without glycine) | Schupp et al. FEMS Microbiology Lett. (1986), 36, 159–162 |
| NL19Q | Schupp et al. FEMS Microbiology Lett. (1987), 42, 135–139 |
| SCR12mod | 20 g/l full-fat soya flour<br>20 g/l saccharose<br>12 g/l HEPES<br>0.1 g/l SAG 471 antifoam<br>adjust pH to 7.5 with NaOH before sterilisation (autoclaving) |
| SET | 75 mM NaCl, 25 mM EDTA, 20 mM Tris, pH 7.5 |

Example 1

Obtaining High-molecular-weight Genomic DNA Fragments from S. longisporoflavus

In order to obtain high-molecular-weight genomic DNA from S. longisporoflavus, cells of the strain S. longisporoflavus R19 DSM 10189 are cultured for 24 hours at 28° C. in SCR12mod medium. 5 ml of the culture are then transferred to 100 ml of NL148 medium (+2.5 g/l glycine) in a 500 ml Erlenmeyer flask and the culture is incubated for 48 hours at 28° C. The cells are separated from the medium by centrifuging at 3000 g for 10 min. and are resuspended in 5 ml of SET (75 mM NaCl, 25 mM EDTA, 20 mM Tris, pH 7.5). The extraction of high-molecular-weight chromosomal DNA is effected in accordance with the method of A. Pospiech and J. Neumann (Trends in Genetics (1995), 11, 217–218).

The high-molecular-weight genomic DNA of S. longisporoflavus thus isolated is partially digested in portions of approximately 5 µg of DNA using the restriction enzyme Sau3A (Boehringer, Mannheim), forming DNA fragments the majority of which are from 5 to 40 kb in size. The requisite amount of enzyme, in a range of from 0.002–0.02 units/µg of DNA, is determined empirically by analysis of the digestion (37° C., 30 minutes) using agarose gel electrophoresis. The enzyme reaction is stopped by incubation for 15 minutes at 65° C., followed by phenol/chloroform extraction and ethanol precipitation.

The DNA thus pretreated is separated according to fragment size by centrifuging (83000 g, 20° C.) for 18 hours over a 10% to 40% saccharose density gradient. The gradient is fractionated in aliquots of 0.5 ml and dialysed. 10 µl samples are analysed on a 0.3% agarose gel using a DNA size standard. Fractions containing chromosomal DNA of the desired size are collected, precipitated with ethanol and concentrated.

Example 2

Cloning of Random DNA Fragments of S. longisporoflavus R19 (DSM 10189) into Plasmid Vector pIJ486

For cloning S. longisporoflavus DNA fragments, the generally known Streptomyces plasmid vector pIJ486, which has a wide range of hosts and is present in a large number of copies per cell (Ward et al., Mol. Gen. Genet. (1986), 203, 468–478), is used. The vector is first transformed into S. longisporoflavus R19 using the general transformation conditions for Streptomyces described in Hopwood et al. (Genetic manipulation of Streptomyces, a laboratory manual. The John Innes Foundation, Norwich (1985) pages 110–111). For further work with S. longisporoflavus, the plasmid pIJ486 is isolated from S. longisporoflavus using a CsCl preparation. For that purpose, cells of S. longisporoflavus containing pIJ486 are cultured for 48 hours at 28° C. in NL19Q medium. Then 10×2.5 ml of culture are used to inoculate 200 ml Erlenmeyer flasks with 50 ml of nutrient solution NI148 each, and incubated for 48 hours at 28° C. pIJ486 plasmid DNA is then isolated from the 500 ml of culture solution; Hopwood et at (pages 82–84).

In order to clone S. longisporoflavus DNA fragments, the vector pIJ486 is cleaved completely with the restriction enzyme BamHI, precipitated with ethanol and then treated with alkaline phosphatase (Boehringer, Mannheim) in accordance with the manufacturer's instructions, in order to prevent self-ligation of the plasmid in the subsequent ligation reactions. The vector thus treated is ligated with partially Sau3A-digested chromosomal DNA of S. longisporoflavus (fraction after sucrose gradient with DNA fragments of 5–20 kb, see above). The ligation is effected with T4-DNA ligase (Boehringer, Mannheim) in accordance with the manufacturer's instructions and with approximately equimolar amounts of the two DNA starting materials and a final concentration of total DNA of approximately 600 mg/ml in a ligation volume of 10 ml. 1 ml of the ligation batch is used to transform the S. longisporoflavus mutant M14, which is blocked in the final step of staurosporin biosynthesis and produces the staurosporin analogue 3'-demethyl-3'hydroxystaurosporin (Hoehn et al, J. Antibiotics (1995), 48, 300–305), using the general transformation conditions for Streptomyces described in Hopwood et al. (pages 110–111). The transformation batch is then plated out onto R2YE agar (Hopwood et al., page 236). In order to select the colonies containing the plasmid, after 20 hours 30 µg/ml of thiostreptone (final concentration) are poured over the plates. For the plasmid preparation, 24 thiostreptone-resistant colonies are each transferred into 25 ml of TSB medium containing 30 µg/ml of thiostreptone (50 ml Erlenmeyer flasks, each containing 10–20 sterile quartz splinters in order to produce short mycelium fragments) and incubated for 48 hours at 28° C. The plasmids are then isolated from those cultures using a slight modification of the method of Birnboim and Doly (Nucl. Acids Res. (1979), 7, 1513–1523). The method is modified as follows: lysozyme digestion for 60 minutes at 30° C. in the following solution: 2 mg/ml of lysozyme, 10 mM EDTA, 25 mM tris pH 8.0, 10% glucose). Analysis of the plasmids shows that approximately 60% of the transformed colonies contain a 5–20 kb DNA fragment, integrated in the plasmid.

Example 3

Identification and Cloning of a S. longisporoflavus DNA Fragment that Complements the Blocked Mutant M14 Clone for Normal Staurosporin Production 12 300 transformed colonies of the mutant S. longisporoflavus Ml 4 are obtained in several series from the ligation batch described above and analysed for complementation of the blocked staurosporin biosynthesis step. From the investigations carried out above, it can be inferred that 60%, or approximately 7380, of the clones investigated contain plasmid pIJ486, together with an additional DNA fragment of S. longisporoflavus. After incubating the R2YE plates at 28° C. for 6 days, the 12 300 colonies are screened (pretested) as follows in a biological test for staurosporin production:

Biological test: In order to transfer (replica plate) all 12 300 colonies to a different agar, sterile Whatman W541 filter paper is placed on each R2YE agar plate, the plate is incubated overnight at 28° C. and the filter is then removed in a sterile manner and placed carefully on plates containing MM minimal agar (Hopwood et al., page 233). After incubation of the MM plates for 24 hours at 28° C., the filter paper is removed and the plates are incubated for a further 24 hours. Using that procedure, the colonies are transferred 1 to 1 from the original R2YE agar to the MM agar, the original R2YE plates serving at the same time as original plates for the further processing of colonies that exhibit positive results in the biological test. 6 ml of DST soft agar (48° C.) containing approximately $10^7$ cells of *Saccharomyces cerevisiae* ATCC 9763 are poured over each of the MM plates which contain small but visibly replicated colonies. Those plates are incubated overnight at 30° C. and then investigated for inhibition zones (in lawns where the *Saccharomyces cerevisiae* test organism has grown) produced by the *S. longisporoflavus* colonies. Under those test conditions, colonies of *S. longisporoflavus* R19 produce an inhibition zone 2–4 mm in diameter as a result of their staurosporin production, whereas colonies of the blocked mutant M14 do not normally produce an inhibition zone.

In one colony, a significant inhibition zone can be detected using this biological test. That clone is isolated from the original R2YE plate and, in order to isolate the plasmid, transferred into 25 ml of TSB medium containing 30 μg/ml of thiostreptone (50 ml Erlenmeyer flasks, each containing 10–20 sterile quartz splinters in order to produce short mycelium fragments) and incubated for 48 hours at 28° C. The plasmid DNA is then isolated from the culture using a slight modification of the method of Birnboim and Doly (Nucl. Acids Res. (1979), 7,1513–1523) (see above) and analysed. The clone contains small amounts of recombinant plasmid DNA, together with an additional *S. longisporoflavus* DNA fragment of approximately 20 kb. This plasmid preparation is given the number pSLO18/10.

In order to monitor the complementation of the blocking of the mutant *S. longisporoflavus* M14 by the plasmid DNA pSLO18/10, the latter is again transformed into that mutant. It is now found that 3 out of 10 transformed M14 colonies are complemented by the plasmid DNA for approximately normal staurosporin production. The plasmids of those 3 clones are identical (number pSLO18/10/2) and contain an inserted DNA fragment of approximately 20 kb in which an internal 2.1 kb BgIII fragment is detectable.

Example 4

Analysis of the Cloned 2.1 kb BgIII DNA fragments

The first step is to determine whether the identified and cloned 2.1 kb BgIII fragment of *S. longisporoflavus* is sufficient alone to complement the *S. longisporoflavus* mutant M14. For that purpose, the DNA fragment is isolated from the plasmid pSLO18/10/2, subcloned into the vector pIJ486 and transformed into the *S. longisporoflavus* M14 mutant. Analysis of the clones thus obtained reveals that all of the clones that contain the 2.1 kb BgIII DNA fragment are complemented for normal staurosporin production (approximately equivalent to the parent strain R19 of the mutant M14). Cultures in a liquid medium give HPLC values of 100–200 mg/l staurosporin, while the value for the mutant M14 is 0–5 mg/l. The plasmid containing the 2.1 kb BgIII fragment of *S. longisporoflavus* is given the number pSLO24/3.

In order to demonstrate that the 2.1 kb BgIII fragment is a chromosomal *S. longisporoflavus* DNA fragment, the fragment is radioactively labelled with $CTP^{32}P$ (see below) and analysed as a probe in a Southern Blot with BgIII-digested chromosomal DNA of *S. longisporoflavus* R19. The experiment confirms that the cloned 2.1 kb BgIII fragment is an authentic chromosomal fragment of *S. longisporoflavus* R19.

Example 5

DNA Sequence Determination of the 2.1 kb BgIII Fragment

For sequencing, the 2.1 kb BgIII fragment is first isolated from the plasmid pSLO24/3 (Maniatis et al., 1982) and subcloned into the BamHI cleavage site of the vector pUC18 which is suitable for DNA sequencing (pSL26/1=number of the new plasmid). In addition, a 1.1 kb SaII subfragment, which is located internally in the 2.1 kb BgIII fragment, is cloned into vector pUC18 in both orientations (pSLO32/13, pSLO32/19). The DNA of the three plasmids pSLO26/1, pSLO32/13, pSLO32/19 is sequenced using the dideoxy nucleotide chain-termination method of Sanger, with stain-labelled primers, and the Applied Biosystems automatic sequencer (Model 373A) in accordance with the manufacturers' instructions. Universal pUC18 primers and new oligonucleotide primers, constructed in accordance with newly obtained sequences in the two BgIII and SaII fragments, are used for the double-stranded sequencing. The resulting DNA sequences from individual runs are assembled using Applied Biosystems software. In that manner, both DNA strands of the the 2.1 kb BgIII fragment of *S. longisporoflavus* R19 can be fully sequenced. The DNA sequence of the 2.1 kb BgIII fragment, which is 2122 base pairs in length, is set out in SEQ ID NO 1.

Example 6

Analysis of 2 Regions (Genes) Coding for Proteins on the 2.1 kb BgIII Fragment

The nucleotide sequence of the 2.1 kb BgIII fragment is analysed using the computer program Codonpreference (Genetics Computer Group 1994). The analysis shows that two distinct open reading frames (ORF), each coding for one protein, are present. The codons used in the two ORFs are typical for Streptomyces genes, from which it may be deduced that there are two genes on the 2.1 kb BgIII fragment of *S. longisporoflavus*. A comparison of the two genes of *S. longisporoflavus* and of the proteins derived therefrom with DNA/protein sequences from the GenBank/EMBL data bank yields the following results:

Gene 1 (ORF of base pair 845–1684; SEQ ID NO 2): codes for a protein containing 280 amino acids. The protein is significantly similar to known S-adenosyl methionine-dependent methyl transferases, especially to those of Streptomyces and Actinomyces, which are involved in the transfer of methyl groups in secondary metabolite biosyntheses. In particular, the protein derived from gene 1 has the three typical sequence motifs that are characteristic of such methyl transferases. A comparison of the motif 1 sequences is given here as an example:

| Microorganism | Gene | Sequence | Product |
|---|---|---|---|
| S. longisporoflavus | | VLDLGCGVG | staurosporin O-MT SEQ ID NO: 6 |
| S. erythraea | eryG | VLDVGFGLG | erythromycin O-MT SEQ ID NO: 7 |
| S. peuceticus | dnrK | VLDVGGGKG | carminomycin O-MT SEQ ID NO: 8 |
| S. mycarofaciens | mdmC | VLEIGTGTG | midamycin O-MT SEQ ID NO: 9 |
| S. glaucescens | tcmO | FVDLGGARG | tetracenomycin O-MT SEQ ID NO: 10 |
| Consensus O-MT general | | VLDIGGGTG SEQ ID NO: 11 | |

As demonstrated above, the 2.1 kb BgIII fragment of *S. longisporoflavus* is capable of complementing the mutant M14 which is blocked in precisely such a methyl transferase step in the biosynthesis of staurosporin. That finding, together with the sequence analysis, which showed significant homology between the gene product of gene 1 of the BgIII fragment and methyl transferases, leads to the definite conclusion that gene 1 codes for a methyl transferase that is responsible for the O-methylation step from 3'-demethoxy-3'-hydroxystaurosporin to staurosporin in the biosynthesis of staurosporin.

Gene 2 (ORF of base pair 148–768; SEQ ID NO: 3): codes for a protein containing 207 amino acids. The protein is significantly similar to the dTDP-4-keto-6-deoxyglucose 3,5-epimerase of *Streptomyces glaucescens*, that is to say there is 48.6% amino acid identity over a region of 148 amino acids. The dTDP-4-keto-6-deoxyglucose 3,5-epimerase of Streptomyces is involved in the synthesis of the deoxy sugar moiety of metabolites, such as streptomycin. Since staurosporin also has a deoxy sugar moiety in the molecule, it may be concluded that gene 2 of the 2.1 kb BgIII fragment is involved in the synthesis of that moiety of the staurosporin molecule.

The above assumption regarding gene 2 made as a result of the sequence comparison can be confirmed by the fact that the *S. longisporoflavus* mutant M13 (Hoehn et al, J. Antibiotics (1995), 48, 300–305), which is blocked in a synthesis step of the deoxy sugar moiety of staurosporin, can be complemented for normal staurosporin production by the 2.1 kb BgIII fragment. Gene 2 of the 2.1 kb fragment of *S. longisporoflavus* is thus involved in a biosynthesis step in the deoxy sugar moiety of staurosporin.

Example 7

Construction of a Cosmid Gene Bank of *S. longisporoflavus* R19

The commercially available plasmid pWE15 (Stratagene, La Jolla, Calif., USA) is used as the cosmid vector. pWE15 is cleaved completely using the enzyme BamHI (Maniatis et al. 1989) and precipitated with ethanol. The cosmid DNA is ligated with the corresponding size-fractionated *S. longisporoflavus* Sau3A DNA fragments (see above) with the aid of a T4-DNA ligase. During the ligation, approximately 3 µg each of the two DNA starting materials are used in a reaction volume of 20 µl, and the ligation is carried out for 15 hours at 12° C.

Using the in vitro packaging kit commercially available from Stratagene (La Jolla, Calif., USA), 4 µl of the above ligation batch are packaged in lambda phages (in accordance with the manufacturer's instructions). The resulting phages are introduced into the *E. coli* strain X-1 BlueMR® (Stratagene) by means of infection. Titration of the phage material yields approximately 20 000 phage particles per ml and an analysis of 12 cosmid clones shows that all the clones contain 30–40 kb plasmid DNA inserts.

Example 8

Preparation of a Radioactive Probe of the 2.1 kb BgIII Fragment of *S. longisporoflavus*

The plasmid pSL26/1, which contains the 2.1 kb BgIII fragment in the *E. coli* vector pUC18, is used as the starting material for the preparation of the DNA probe. The 2.1 kb insert fragment is separated off by means of EcoRI+HindIII digestion and then separated using agarose gel. Approximately 1 µg of the isolated 2.1 kb DNA fragment is radioactively labelled with $^{32}$P-d-CTP by means of the nick-translation system from GIBCO/BRL (Basle) in accordance with the manufacturer's instructions.

Example 9

Isolation of Four Cosmid Clones with Chromosomal *S. longisporoflavus* DNA Fragments Containing the 2.1 kb BaIII Fragment By infection of *E. coli* X-1 Blue MR® (Stratagene) with an aliquot of the in vitro-packaged lambda phages (see above), over 4000 clones are obtained on a plurality of LB+ampicillin+neomycin plates (50 μg/ml of each). The clones are tested by colony hybridisation on nitrocellulose filters (Schleicher+Schuell). The $^{32}$P-d-CTP radioactively labelled 2.1 kb *S. longisporoflavus* fragment prepared above is used as DNA probe.

6 cosmid clones are found that exhibit a significant signal with the DNA probe. The plasmid DNA of those cosmids is isolated (Maniatis et al 1989), digested with BglII and analysed in an agarose gel. The analysis shows that all 4 recombinant plasmids contain inserted chromosomal *S. longisporoflavus* DNA approximately 35 kb in size and all 6 contain the 9.1 kb BglII fragment.

Example 10

Characterisation of the Chromosomal *S. longisporoflavus* DNA Region Adjacent to the Cloned BglII Fragment In order to characterise the chromosomal *S. longisporoflavus* DNA region adjacent to the cloned BglII fragment, a restriction analysis of the plasmid DNA of one of the 6 cosmid clones is carried out. The selected plasmid of the cosmid clone has the number pNE29 (DSM 10188).

In order to identify the fragments that overlap with the BglII fragment, the plasmid pNE29 is digested with enzymes EcoRI, PvuI, PvuII and BclI and tested in a Southern Blot (Maniatis et al. 1989) with the 2.1 kb fragment as probe. The result of the analysis is that in each case 2 or 1 DNA fragment(s) of the following size overlap(s) with the 2.1 kb fragment: EcoRI: >20 kb, PvuII: 3.5 kb and 6.5 kb; PvuI: 3.4 kb and 2.1 kb; BclI: 3.6 kb. An approximately 10 kb DNA region of the chromosome of *S. longisporoflavus* can thus be characterised (FIG. 1).

By means of a further restriction analysis of the plasmid pNE29, a rough restriction map of that region of the *S. longisporoflavus* chromosome can be prepared which allows the approximately 35 kb DNA region to be characterised. The restriction map is shown in FIG. 2.

Example 11

DNA Sequence Determination of the 6 kb PvuII-BglII Fragment Immediately Preceding the Sequenced 2.1 kb BglII Fragment (see FIG. 1)

The 6 kb PvuII-BglII fragment immediately preceding the sequenced 2.1 kb BglII fragment (on the left in FIG. 1) is sequenced using the 6.5 kb PvuII fragment from the approximately 10 kb region of the S. longisporoflavus chromosome characterised in Example 10. For that purpose, the 6.5 kb PvuII fragment is isolated from cosmid pNE29 or cosmid pNE31 (one of the 4 cosmids from Example 9), which is identical in that region (Maniatis et al., 1982), and subcloned into the SmaI cleavage site of the vector pBluescript II SK (Stratagene) suitable for DNA sequencing (pNE37=number of the new plasmid). In addition, SmaI subfragments located internally in the 6.5 kb PvuII fragment are cloned into the SmaI cleavage site of the vector pBluescript II SK. The DNA sequencing is effected with the plasmids using the dideoxy nucleotide chain-termination method of Sanger, as described in Example 5. Universal pBluescript primers and new oligonucleotide primers, constructed in accordance with newly obtained DNA sequences, are used for the double-stranded DNA sequencing. The resulting DNA sequences are joined together and analysed using software from Applied Biosystems and the Genetics Computer Group (1994). In that manner the complete DNA sequence of the 6 kb PvuII-BglII fragment of S. longisporoflavus can be determined. That DNA sequence is set out in SEQ ID NO 4. The resulting sequence of the 0.5 kb BglII-PvuII region of the 6.5 kb PvuII fragment shows that the two DNA sequences SEQ ID NO 1 and SEQ ID NO 4 of S. longisporoflavus are connected to one another directly via the BglII cleavage site.

Example 12

Analysis of 5 Regions (Genes) Coding for Proteins on the 6.5 kb PvuII Fragment of S. longisporoflavus (see FIG. 1)

The nucleotide sequence of the 6.5 kb PvuII fragment is analysed using the computer program Codonpreference (Genetics Computer Group 1994). The analysis shows that 5 distinct open reading frames (ORF) that code for proteins are present. The codons used in the ORFs are typical for Streptomyces genes, from which it can be deduced that there are 5 genes on the 6.5 kb PvuII fragment of S. longisporoflavus. A comparison of the 5 genes of S. longisporoflavus and the proteins derived therefrom with DNA/protein sequences from the gene/EMBL data bank yields the following results:

Gene 1 (ORF of base pair 378–1655 of SEQ ID NO 4) codes for a protein containing 425 amino acids.

Gene 2 (ORF of base pair 1747–2553 of SEQ ID NO 4) codes for a protein containing 268 amino acids. The protein is significantly similar to known S-adenosyl methionine-dependent methyl transferases, especially to those of Streptomyces and Actinomyces, which are involved in the transfer of methyl groups to secondary metabolites. On the basis of that similarity it can be concluded that the methyl transferase is involved in the N-methylation step of the sugar in staurosporin biosynthesis.

Gene 3 (ORF of base pair 2593–4011 of SEQ ID NO 4) codes for a protein containing 472 amino acids.

Gene 4 (ORF of base pair 4013–4999 of SEQ ID NO 4) codes for a protein containing 328 amino acids.

Gene 5 (ORF of base pair 5071–6171 of SEQ ID NO 4) codes for a protein containing 366 amino acids. That protein is significantly similar to amino transferase enzymes, such as the DnrJ protein of Streptomyces peuceticus. Those enzymes, which are involved in the biosynthesis of antibiotics, are ascribed the function of adding an amino group in the biosynthesis of the deoxyamino sugar moiety of the antibiotic. On the basis of that similarity, it can be concluded that gene 5 is involved in the synthesis of the deoxyamino sugar in the biosynthesis of staurosporin.

Example 13

DNA Sequence Determination of the 1.8 kb BglII-PvuII Region Immediately Following the Sequenced 2.1 kb BglII Fragment (Corresponds to the Right-hand BglII-PvuII End Fragment in FIG. 1)

The approximately 1.8 kb BglII-PvuII region to the right of the sequenced 2.1 kb BglII fragment (FIG. 1) is sequenced using the 3.5 kb PvuII fragment from the approximately 10 kb region of the S. longisporoflavus chromosome characterised in Example 10. For that purpose, the 3.5 kb PvuII fragment is isolated from cosmid pNE29 or cosmid pNE31 (one of the 4 cosmids from Example 9), which is identical in that region (Maniatis et al., 1982), and subcloned into the SmaI cleavage site of the vector pBluescript II SK (Stratagene) which is suitable for DNA sequencing (pNE36=number of the new plasmid). In addition, SmaI subfragments located internally in the 3.5 kb PvuII fragment are cloned into the SmaI cleavage site of the vector pBluescript II SK. The DNA sequencing is carried out with the plasmids using the dideoxy nucleotide chain-termination method of Sanger, as described in Example 5. Universal pBluescript primers and new oligonucleotide primers, constructed in accordance with newly obtained DNA sequences, are used for the double-stranded DNA sequencing. The resulting DNA sequences are joined together and analysed using software from Applied Biosystems and the Genetics Computer Group (1994). In that manner the complete DNA sequence of the 1.8 kb BglII-PvuII region of S. longisporoflavus can be determined. The overlaps between the resulting sequences of the whole 3.5 kb PvuII fragment used for the sequencing and SEQ ID NO 1 (2.1 kb BglII fragment) show that the 2.1 kb BglII and 1.8 kb BglII-PvuII DNA regions of S. longisporoflavus shown in FIG. 1 are connected not directly, but via a BglII fragment having only 69 base pairs. The entire DNA sequence from immediately adjacent to the right-hand side of the 2.1 kb BglII fragment to the next PvuII cleavage site (right-hand end in FIG. 1) is set out in SEQ ID NO 5. Taken together, the DNA sequences SEQ ID NO 4, SEQ ID NO 1 and SEQ ID NO 5 thus represent the DNA sequence of the region of S. longisporoflavus shown in FIG. 1.

Deposited Microorganisms

The following microorganisms and plasmids have been deposited with the "Deutsche Sammlung von Mikroorganismen und Zellkulturen GmbH (DSM)" (German Collection of microorganisms and cell cultures), Mascheroder Weg 1 b, D-38124 Brunswick, in accordance with the requirements of the Budapest Convention:

| Microorganism/plasmid | Date of deposition | Deposit number |
|---|---|---|
| *Streptomyces longisporoflavus* | 23.08.95 | DSM 10189 |
| *E. coli*/pNE29 | 23.08.95 | DSM 10188 |

What is claimed is:

1. An isolated DNA fragment comprising a DNA segment having a region encoding a polypeptide contributing to staurosporin biosyntheses, said DNA segment selected from the group consisting of
   a) the 35 kb segment of *Streptomyces longisporoflavus* DSM 10189 inserted in the plasmid vector pNE29 and maintained by the *E. coli* strain DSM 10188,
   b) a 2.1 kb segment of said 35 kb insert defined by the pair of Bg/l restriction endonuclease recognition sites set forth in FIG. 2, and
   c) a chromosomal DNA segment native to a species of Streptomyces capable of staurosporin biosynthesis which hybridizes with a DNA sequence of SEQ ID NO:1 under wash conditions of 55–56° C. in 0.2×SSC.

2. A DNA fragment or a portion thereof according to claim 1, said DNA region comprising a nucleotide sequence selected from the group consisting of a nucleotide sequence encoding the polypeptide of SEQ ID NO 2, a nucleotide sequence encoding the polypeptide of SEQ ID NO 3, and a nucleotide sequence encoding a polypeptide encoded by an ORF of SEQ ID NO 4 or SEC ID NO 5.

3. A DNA fragment or a portion thereof according to claim 2, wherein said nucleotide sequence encoding a polypeptide encoded by an ORF of SEQ ID NO 4 is selected from the group consisting of a nucleotide sequence encoding the polypeptide encoded by the ORF of base pairs 378–1655 of SEQ ID NO 4, a nucleotide sequence encoding the polypeptide encoded by the OFF of base pairs 1747–2553 of SEQ ID NO 4, a nucleotide sequence encoding the polypeptide encoded by the ORF of base pairs 2593–4011 of SEQ ID NO 4, a nucleotide sequence encoding the polypeptide encoded by the ORF of base pairs 4013–4999 of SEQ ID NO 4, and a nucleotide sequence encoded by the ORF of base pairs 5071–6171 of SEQ ID NO 4.

4. A DNA fragment or a portion thereof according to claim 2, said DNA fragment being a nucleotide sequence selected from the group consisting of SEQ ID NO 1, SEQ ID NO 4 and SEQ ID NO 5.

5. A DNA fragment or a portion thereof according to claim 2, said DNA region comprising a 10 kb region having a restriction pattern as depicted in FIG. 1.

6. A hybrid vector comprising a DNA fragment according to claim 1.

7. A hybrid vector comprising an expression cassette comprising a DNA fragment according to claim 1.

8. A host organism comprising a hybrid vector according to claim 7.

9. A host organism into the chromosome of which a DNA fragment according to claim 1 has been integrated.

10. A method of isolating a Streptomyces chromosomal DNA segment which encodes a polypeptide associated with staurosporin biosynthesis wherein a DNA sequence present in SEQ ID NO: 1 is used as a probe in hybridizations conducted with a Streptomyces chromosomal DNA library.

11. A method for inhibiting staurosporin biosynthesis comprising disrupting a Streptomyces gene which encodes a polypeptide associated with staurosporin biosynthesis wherein a DNA sequence present in SEQ ID NO:1.

12. A method for performing PCR amplification comprising the step of; of isolating a Streptomyces chromosomal DNA segment which encodes a polypeptide associated with staurosporin biosynthesis wherein a DNA sequence comprising PCR amplification of Streptomyces spp. chromosomal DNA with a DNA sequence present in SEQ ID NO: 1 or nucleic acid complementary to the nucleic acid of SEQ ID NO: 1.

13. A method for producing staurosporin from 3'-demethyl-3'hydroxystaurosporin wherein a Streptomyces host cell deficient in staurosporin biosynthesis is transformed with a DNA sequence of SEQ ID NO: 1, obtaining isolated nucleic acid from the transformed host, and producing staurosporin therefrom.

* * * * *

UNITED STATES PATENT AND TRADEMARK OFFICE
CERTIFICATE OF CORRECTION

PATENT NO. : 6,210,935 B1  
APPLICATION NO. : 09/029603  
DATED : April 3, 2001  
INVENTOR(S) : Schupp et al.

Page 1 of 1

It is certified that error appears in the above-identified patent and that said Letters Patent is hereby corrected as shown below:

Column 36
  Line 47, Claim 3, "OFF" should read -- ORF --.

Signed and Sealed this

Sixth Day of November, 2007

JON W. DUDAS  
*Director of the United States Patent and Trademark Office*

SEQUENCE LISTING

<160> NUMBER OF SEQ ID NOS: 11

<210> SEQ ID NO 1
<211> LENGTH: 2122
<212> TYPE: DNA
<213> ORGANISM: Streptomyces longisporoflavus
<220> FEATURE:
<221> NAME/KEY: misc_RNA
<222> LOCATION: (1)..(2122)
<223> OTHER INFORMATION: product = 2.1 kb region

<400> SEQUENCE: 1

```
ggatcttctc gctgccgatg taccctcgc tcgccccga cctccaggac aaggtcatcc        60
acgccgtacg cgaggtgctc gccactctgt gactgtccgt caactctctt atcgcatcgc       120
gtcgttcacc gagtcactgg agcagaagtg aaagcacgcc cgctcaccgt cgagggagcc       180
gtcgagttca ccccccgcgt cttccccgac gacaggggca agttcgtctc gccgtaccag       240
gaagcgacgt tcaccgaggc ccacggcacc ccgctcttcc ccgtggcgca gaccaaccac       300
agcgtgtccc ggcgaggtgt cgtacgcggc gtccactaca cggcgacgcc cccgggcacc       360
gccaagtacg tctactgcgc ccgaggccgc gccctgaca tcgtcgtcga catccgcgtc       420
ggctcgccca ccttcggccg ctgggacgcg gtgctgatgg accagctgga tcaccgggcc       480
agctattttc ccgtcggggt cggccatgcc ttcgtggccc tggaggacga caccgacatg       540
tcgtacatgc tctccgggcg ctatgtcgcc gagcacgaac tctccctgtc cgccctggac       600
ccggacctcg gctgccgat ccccacggac ctcgaaccga tcctctccga acgcgaccgc       660
gcggccgtca ccctcgccga ggcccaggag aagggcctgc tgccggacta cgcccgctgc       720
caggagatcg agcggggact cgtccccgc gcgaggccgg cggcgtagcc ccgcaccgac       780
gaggcatttc actcccctcc tcactccctt tctcactgtc gatcgatccg aaaggccgtt       840
cccatgaccg actccaccca gaccctgccc gtgccggaag ccgtcggtga gctgtacgac       900
cggctgacgc tgagcgcgat gaacgacggc tcgttcaacc ccaatgtgca catcggctat       960
tgggacaccc cggctccga ggccaccatc gaggaggcga tggaccggct caccgatgtg      1020
ttcatcgaac ggctgaacgc gtacgccacc tcccacgtcc tcgacctcgg ctgcggggtg      1080
ggcgggcccg gcctcaggt cgtggcgcgc accggggcac gggtcaccgg catcagcatc      1140
agcgaggagc agatcaggac cgccaaccgg ctggccgccg aggccggggt cgccgaccgt      1200
gccgtgttcc agcatggcga cgcgatgaaa ctgcccttcg ccgacgcctc gttcgacgcc      1260
gtgatggcgc tggagtcgat ctgccacatg cccgaccggc agcaggtgtt caccgaggtg      1320
tgccgggtgc tgcgcccgg gggccggatc gtcctcaccg acatcttcga gcgccacccg      1380
cgcaaggcgg tacgacaccc cggcatcgac aagttctgcc gcgacctgat gtcgaccacg      1440
gcggacatcg acgactacgt ggcgctgctg caccgctccg ggctgcggct gcgcgagatc      1500
```

```
gtcgacgtca ccgagcagac cacgctgcgc ctcgccgacg agatcggcag gctcgcggcc  1560
gtcgaggagc gccccgtggc catggacgag ggcaacttcg ccttcggcga cgactccttc  1620
aagccgtccg acctggcggg cgtcgacgac ttcggctgcc tcctggtcac cgccgagcgc  1680
ccctgacccg ctgaaacgcc gggaggtcag gcgcacctgc cctccggcg cccgtccccc   1740 gggtcgcgag cgcattgcat ccccgtgcc gcgagcccac gcattcccg gccacgagc    1800 ccacgcgtcc gcgacacgga cccacaagga gaggcaagaa cgagatgacg cattccggtg  1860
agcggaccga tgtgctgatc gtgggcggcg gcccggtcgg gatggcgctg gcgctggatc  1920
tgaggtaccg gggcatcgac tgtctggtcg tcgacgccgg tgacggcacg gtccggcacc  1980
ccaaggtcag caccatcggt ccccgctcga tggaactctt ccgccgctgg ggcgccgcgg  2040
acgcgatccg gaacgccggc tggcccgccg accatcccct ggacatcgcc tgggtgacca  2100
aggtcggcgg ccacgaagat cc                                          2122
```

<210> SEQ ID NO 2
<211> LENGTH: 280
<212> TYPE: PRT
<213> ORGANISM: Streptomyces longisporoflavus
<220> FEATURE:
<223> OTHER INFORMATION: methyl transferase-like protein

<400> SEQUENCE: 2

```
Met Thr Asp Ser Thr Gln Thr Leu Pro Val Pro Glu Ala Val Gly Glu
 1               5                  10                  15

Leu Tyr Asp Arg Leu Thr Leu Ser Ala Met Asn Asp Gly Ser Phe Asn
            20                  25                  30

Pro Asn Val His Ile Gly Tyr Trp Asp Thr Pro Gly Ser Glu Ala Thr
        35                  40                  45

Ile Glu Glu Ala Met Asp Arg Leu Thr Asp Val Phe Ile Glu Arg Leu
    50                  55                  60

Asn Ala Tyr Ala Thr Ser His Val Leu Asp Leu Gly Cys Gly Val Gly
65                  70                  75                  80

Gly Pro Gly Leu Arg Val Val Ala Arg Thr Gly Ala Arg Val Thr Gly
                85                  90                  95

Ile Ser Ile Ser Glu Glu Gln Ile Arg Thr Ala Asn Arg Leu Ala Ala
            100                 105                 110

Glu Ala Gly Val Ala Asp Arg Ala Val Phe Gln His Gly Asp Ala Met
        115                 120                 125

Lys Leu Pro Phe Ala Asp Ala Ser Phe Asp Ala Val Met Ala Leu Glu
    130                 135                 140

Ser Ile Cys His Met Pro Asp Arg Gln Gln Val Phe Thr Glu Val Cys
145                 150                 155                 160

Arg Val Leu Arg Pro Gly Gly Arg Ile Val Leu Thr Asp Ile Phe Glu
                165                 170                 175

Arg His Pro Arg Lys Ala Val Arg His Pro Gly Ile Asp Lys Phe Cys
            180                 185                 190

Arg Asp Leu Met Ser Thr Thr Ala Asp Ile Asp Tyr Val Ala Leu
        195                 200                 205

Leu His Arg Ser Gly Leu Arg Leu Arg Glu Ile Val Asp Val Thr Glu
    210                 215                 220

Gln Thr Thr Leu Arg Leu Ala Asp Glu Ile Gly Arg Leu Ala Ala Val
225                 230                 235                 240

Glu Glu Arg Pro Val Ala Met Asp Glu Gly Asn Phe Ala Phe Gly Asp
                245                 250                 255
```

```
Asp Ser Phe Lys Pro Ser Asp Leu Ala Gly Val Asp Phe Gly Cys
            260                 265                 270

Leu Leu Val Thr Ala Glu Arg Pro
        275                 280

<210> SEQ ID NO 3
<211> LENGTH: 206
<212> TYPE: PRT
<213> ORGANISM: Streptomyces longisporoflavus
<220> FEATURE:
<223> OTHER INFORMATION: NDP-4-keto-6-deoxyhexose 3,5-epimerase-like
      protein

<400> SEQUENCE: 3

Val Lys Ala Arg Pro Leu Thr Val Glu Gly Ala Val Glu Phe Thr Pro
  1               5                  10                  15

Arg Val Phe Pro Asp Asp Arg Gly Lys Phe Val Ser Pro Tyr Gln Glu
             20                  25                  30

Ala Thr Phe Thr Glu Ala His Gly Thr Pro Leu Phe Pro Val Ala Gln
         35                  40                  45

Thr Asn His Ser Val Ser Arg Arg Gly Val Val Arg Gly Val His Tyr
     50                  55                  60

Thr Ala Thr Pro Pro Gly Thr Ala Lys Tyr Val Tyr Cys Ala Arg Gly
 65                  70                  75                  80

Arg Ala Leu Asp Ile Val Val Asp Ile Arg Val Gly Ser Pro Thr Phe
                 85                  90                  95

Gly Arg Trp Asp Ala Val Leu Met Asp Gln Leu Asp His Arg Ala Ser
            100                 105                 110

Tyr Phe Pro Val Gly Val Gly His Ala Phe Val Ala Leu Glu Asp Asp
        115                 120                 125

Thr Asp Met Ser Tyr Met Leu Ser Gly Arg Tyr Val Ala Glu His Glu
    130                 135                 140

Leu Ser Leu Ser Ala Leu Asp Pro Asp Leu Gly Leu Pro Ile Pro Thr
145                 150                 155                 160

Asp Leu Glu Pro Ile Leu Ser Glu Arg Asp Arg Ala Ala Val Thr Leu
                165                 170                 175

Ala Glu Ala Gln Glu Lys Gly Leu Leu Pro Asp Tyr Ala Arg Cys Gln
            180                 185                 190

Glu Ile Glu Arg Gly Leu Val Pro Arg Ala Arg Pro Ala Ala
        195                 200                 205

<210> SEQ ID NO 4
<211> LENGTH: 6085
<212> TYPE: DNA
<213> ORGANISM: Streptomyces longisporoflavus
<220> FEATURE:
<221> NAME/KEY: misc_RNA
<222> LOCATION: (378)..(1665)
<223> OTHER INFORMATION: ORF
<220> FEATURE:
<221> NAME/KEY: misc_RNA
<222> LOCATION: (1747)..(2553)
<223> OTHER INFORMATION: ORF
<220> FEATURE:
<221> NAME/KEY: misc_RNA
<222> LOCATION: (2593)..(4011)
<223> OTHER INFORMATION: ORF
<220> FEATURE:
<221> NAME/KEY: misc_RNA
<222> LOCATION: (4013)..(4999)
<223> OTHER INFORMATION: ORF
<220> FEATURE:
```

```
<221> NAME/KEY: misc_RNA
<222> LOCATION: (5071)..(6085)
<223> OTHER INFORMATION: ORF

<400> SEQUENCE: 4
tgatggccca gcacttcggc gagtgcccgg acgccagtct gcggcggtcg gacctgatga      60
acggggcgat cgacatgatg acgggcctga tgcggccgct ggcggaactg ctcgtcaccc     120
tgccgtcggg gcgccggggc atgaccgccg gaccgtcctt cgaactgccc gagcagcccg     180
cgcccgtgtc ccgaccggac gtggccagac gcggtatcgc ccgccgcctc gacgacctcg     240
cggcgcagtg cgccaagcat ccgctcgtcc ccccgcgcgt ggcggagatg agcaccttct     300
gggccgaccc cttccgcccg ccgagccgtt agggccggtt gcgaaagggg ccgaacactt     360
ccgaccgaag gagacgcatg ccatccgcga cgctgccgcg gttcgacctc atgggctggg     420
acaaggagga catcgcccac ccctacccgg tctaccggcg ctaccgggag gccgccccgg     480
tccatcgcac ggcggcgggc cccggaaagc ctgacaccta ctacgtgttc acctacgacg     540
acgtggtccg cgtcctgtcc aaccggcggt tcggccgcaa cgcccgcgtg gcctccggcg     600
acaccggccc cgacaccgcg cccgtcccga tcccggccga gcaccgcgcc ctgcggaccg     660
tcgtcgagaa ctggctggtc ttcctcgacc ccccgcgcca caccgaactg cgctccctgc     720
tcaccggcga gttctcaccc tcgatcgtca ccggcctgcg ccccgcatc gccgaactcg     780
cgagcgaact cctggaccgg ctccgagcac accgccggcc cgatctcgtc gagggttcgc     840
ggcgcccctc cccgatcctc gtcatctccg cactgctggg catcccccgc ggaggaccac     900
acctggtgcg cgccaacgcg gtggcccttc aggaggccgg caccacgctc gcgcggcggc     960
cacggtacgc acgggccgag gcggcgtccc aggagttcac ccgctacttc cggcgagagg    1020
tggaccggcg cggcggcgac gaccgcgacg atctgctcac cctcctcgtc cgcgcccggg    1080
acaccggatc accgctcagc gtggacggca tcgtcggcac ctgcgtccat ctgctcaccg    1140
ccggccacga gaccaccacc aactgcctcg ccagggcggt cctcaccctg cgcgcccacc    1200
ctgacgtcct cgacgagctg cgcaccacac cggagtcgac accggcggcc gtcgaagagc    1260
tgatgcggta cgacccgccc gtgcaggcgg tgacgcgctg ggcgtacgag gacatccggc    1320
tcggcgacca cgacatcccg cgcggcagcc gggtggtcgc gctgctgggc tcggcgaacc    1380
gggacccggc gcgcttcccg gctcccgacg tgctggacgt ccaccgcgcc gccgaacggc    1440
aggtgggctt cggcctcgga atccactact gcctcggcgc gaccctggcc cgcgccgagg    1500
ccgagatcgg tctgagggcc ctgctggacg gcatccccgc cctcggccga ggcgcccacg    1560
aggtcgagta cgccgacgac atggtcttcc acggcccgam cggctcctc ctcgacctgc    1620
cggamgccac gtdccctcg gccagccacc cctagccctc ggccacccct cgaccccggc    1680
catcccttgc cctggccacc cctcgacccc ggccctctcg actcgcacca gcaggaaggc    1740
acatccatga cgcagcagtc cgacaccacc gccgactcgg tcggtgaggt gtacgaccag    1800
ttcgccgacg ccgcgccag caccgcgatg ggcggcaaca tccacgtggg gtactgggac    1860
gacgaccccg aggtgccgat cgccgaggcc accgaccggc tcaccgatct cgtcgccgag    1920
cgcctcgcgc tccgccccga ccggcatctg ctggacgtgg gctgcggcat cggcgtgccg    1980
gctctcagga tcgccggagc gcacgacgtc cgcgtcaccg ggatcaccgt cagccagcag    2040
caggtcaccg aggcggccga gcgggcggtg gagtccgatg ccggggccgg ggctctcttc    2100
cggctggcgg acgccatgga cctccccttc gaggacgtct ccttcgacgg cgccttcgcc    2160
atcgagtcgc tgctgcatct gcccgaccag acacccgcgc tcaaggagat ccaccgggtc    2220
```

-continued

```
gtccgccccg gcggccggct cgtcatcgcc gacctgtgtc agcgacagcc gttcaccggc    2280
gccgacaagg aggtgctcga cgggatgctg ctgatgtacg agatcgccgg gatcaacaca    2340
ccctacgagc atcgcgcgcg actggcggag gcgggctggg aactgctgga gctgacggac    2400
atcggtgagc aggtccgcgc ctactacggg catgccgccg ccgcgttccg gggtctcgcc    2460
ggggctctcg acgccggcgc ggcgcagcag atgaacgcgg cggccgacct gatggaggct    2520
tcggagggca tccgcactcc ggttacgtcc tgatcacgcg cagcggtcct gaccggacgg    2580
ggagacctgt gatgtcttct ggtctcggcc cgccgtccgc cgccgtacgc ccgcgtgagg    2640
accgtgcgac ggccgaccgt gtcgccctgt ccgccgcgac cgcccgcgga gcaccggtcg    2700
cggaccgagg aggtgcgggc ctggctggcc gagcggcgcc gggcccatgt gttcgaggtg    2760
acgcggatac cgttcgcgga gctgcggcag tggcggttcg aggagggcac cggcaatctc    2820
gtgcaccgca gcgacggtt cttcaccgtc gagggcatgc atgtcgtcga gtcggacggg    2880
cccttcgggg acggcccgta ccaggagtgg cagcagcccg tcgtccgcca gcccgaagtg    2940
ggcatcctcg gcattctcgc caaggagttc gacggagtgc tgcacttcct gatgcaggcc    3000
aagatggagc cggcaatcc ccgtctgctc cagctctccc cgaccgtgca ggccacccgc    3060
agcaactaca cacgggctca ccggggcacg gacgtcaagc tcatcgacca tttcttccga    3120
cccgaccccg accgggtcct cgtcgacgtc ctgcagtccg aacagggctc gtggttctac    3180
cgcaagtcca atcgcaacat gatcgtggag accgtcgacg acgttcccga actgacgac    3240 ttccgctggc tcaccctcgg ccagatcgcc gaactgctgc acgaggacga cctggtcaac    3300
atgaacgcca ggacggtgct gtcgtgcgtg cagtaccccg acacctcgcc cggggcgctg    3360
ctctccgacg cccagctcct gtcctggttc accggggagc gttcccggca cgacatccgc    3420
gtggaggcgg tgccgctcgc tccgtgcgcg gcctggaagc agggtgtcga ggcgatcgag    3480
cacgagaacg ggcgctactt caaggtcgtc gccgtctccg tgcgggccgg caaccgcgag    3540
gtggtcgact gggaccagcc gttgctggag ccggtgggcc tggggtcag cgccttcctg    3600 gtgcgcgaga tcgagggcgt accccatgtc ctggtccatg cccaggccga gggcgggttc    3660
ctggacaccg tcgagctggc tccgaccgtc cagtgcacac ccggcaatta cgcccatctc    3720
accccggagc accgccgcc gttcctcgac accgtcctcg acgcccgccc cgagcgcatc    3780
cgctacgagg ccgtccactc cgaggagggc ggacgcttcc tcaacgccag gagccgctat    3840
ctgctggtcg acgccgacga cgtcccctc gccccgcccc ccggctacac ctgggccacc    3900
ccgggccagc tcaggaccct cacccggcac ggccactacc tgaacgtcga ggcccgcacg    3960
ctgctggcct gcgtcaacgc gacggccgca gggccgcgag gaggacagtg acatgggaa    4020 ccaccgctg atcaccgtgc tcggtgcctc gggtttcgtc gggtcggccg tcacccgggc    4080
gctggcgtcc cggcccgtcc ggctccggct cgtctcccgt cggccctgcg tccctcccc    4140 cggcccggcc gagaccgatg tcgtcaccgc cgatctcacc gaccgggccg cctggccgg    4200 ggcggtgcag ggttcggacg gggtgatcca tctgctgctg ggggagggcg gctggcgggc    4260
agccgagtcc gaccccggtg ccgagcacgt caacgtcggc gtcatgcggg acctcgtcga    4320
ggtactgcgg cccgcgcccg gcgacgcggc accccgctg tggtgtacg ccggtgccgc    4380 ctcgcaggtc ggggtgccgc cccgggagcc cctcgacggc agcgagcccg accgcccgga    4440
gaccgcctac gaccggcaga aactgaccgc tgaacacctc ctgctcaagg ccaccgccga    4500
gggccgggta cgcggcatcg gcctgcgtct gcccaccgtg ttcggcgaga gcacggcgtc    4560
```

```
cggcaccggc gaccgaggcg tcgtgtcggc catggcgcgc aagggccctcg acgggcagac    4620 gctcaccatg tggcacgacg gcaccgtgcg ccgcgacctg gtccatgtcg acgatgtcgc    4680
ggcggcgttc acggccgccc tcgaccaccc ggacgccctc gtgggcggcm attggctgat    4740
cggggccggc cggggcgacg cgctcggcga tgtcttccgg ctgatcgccc tcaccgcggc    4800
cgatgtcctc gggcggtccc cggtcgacgt ggtctccgta gaaccgcccg cgcacgcccc    4860
cgtgaccgac ttccgcagcg tcaccctcga ctcctcgcgt tccgcgcggc accggttgg    4920 cgcccccgga atctccctgc ccgagggcgt gcgccgcacc gtcaccgccc tggcccggga    4980
gcgggccgcg agccggtgac gtcagcgccc ccgaccccta ctcaccacag gcgtacggcc    5040
gtgcgcccgc agtactggaa aggctggacg atgaccacgc gtgtatggga ctacctggcg    5100
gagtaccgag ccgagcgggc ggacatcctc gacgccgtcg aaacggtctt cgagtcgggc    5160
cagttggtgc tcggcgcgag tgtgcgcggc ttcgaggagg agttcgccgc ataccacgga    5220
gtggaccact gcgtgggtgt cgacaacgga acgaacgcca tcaagctcgc tctccaggcc    5280
ctcggggtcg gccccggcga cgaggtgatc acggtgtcca acaccgccgc ccccaccgtc    5340
gtcgccatcg actccaccgg cgccacccc gtcttcgtcg acgtccgcga ggacgacttc    5400
ctcatggaca cgagccaggt cgaggcgcc gtcaccgaac gcaccgctg cctgctcccg    5460 gtccacctgt acgccagtg cgtcgacatg gcgccgctga aggagatcgc cgcccggcac    5520
gtggtcgtcc tggaggactg cgcccaggcc catggccgac agggcgacac catggccggc    5580
accaccggtg acgccgccgc cttctccttc tacccgacca aggtcctcgg cgcgtacggc    5640
gacggcggcg ccacgatcac cggcgacgcg tccgtggccg cccgcctgcg acgcctgcgc    5700
tactacggca tggacgagcg ctactacacc ctggagaccc ccgcccacaa cagccgcctg    5760
gacgaactcc acgcagagat cctccgccgc aaacttcggc gcctcgacac ctacgtcaag    5820
ggccgccgcg ccgtcgccga acgctacgcc gacgggctcg ccgacaccga cctcgtcctg    5880
ccgcacacgg tccccggcaa cgagcacgtc tactacgtgt acgtcgtccg ccaccccgg    5940 cgtgacgaca tcatcgagcg cctcaaggcc cacgacgtcc acctcaacat cagctatccg    6000
tggccggtgc acaccatgac gggcttcgcc cacctcggct acgcaagggc tcgctcccgg    6060
tcaccgaggc actggcgcga gatct                                          6085

<210> SEQ ID NO 5
<211> LENGTH: 1845
<212> TYPE: DNA
<213> ORGANISM: Streptomyces longisporoflavus

<400> SEQUENCE: 5
agatctaccg ctaccggcga ggcacggccg cgaaccgccc ggccttcgtc catacccccg      60
agcccgatca gatctgcccc gcccactggc tcaacccggt gctgatcgag gccgtgggcg     120
tccacccgga cggccccctg ctactgagta cgaccgtcga cggcgtggtc cagaccgacg     180
accacgtcga ggccaccctc accgaccacg ccaccggcac caccggcacc gtccgggcac     240
gcttcctcgt cgcctgtgac ggcgcctcct cgcccgtccg ccggcgctgc ggcatcgagg     300
caccggcccg ccaccgtacg caggtcttcc gcaacatcct cttccgcgcc ccgagctca     360 aggaccgcct gggcgagcgg gccgccctgg tccacttcct gatgctgtcg tccaccgtgc     420 gcttcccccct gcgctcgctg aacggcagcg acctgtacaa cctggtcgtg ggcgccgacg     480
acgacaccgg cgcccgaccc gacgtccctg gccctgcagt gatcaaggac gccctggccc     540
tcgacacccc ggtggagctg ctcggcgaca gcgcgtggcg tctcacccac cgtgtcgccg     600
```

```
accgctaccg ggccggacgg atcttcctcg ccggcgacgc cgcgcacacc ctgtcgccct    660
ccggcggctt cggcctcaac accggtatcg gcgacgccgc cgatctcggc tggaagctcg    720
ccgccaccct ggacggctgg gccggcggc acctcctcga cacctacgac agcgagcgtc    780
gaccgatcgc cgaggagagc ctgaacgagg cccacgacaa tcttcggcgc accatgaaac    840
gggaggtccc gccggagatc cacctcgacg gacccgaggc gagcgggcc cgcgccgtga    900 tggccaggcg cctcgagaac agcggcgcgc ggcgggagtt cgacgcccg cagatccact    960 tcggactgcg ctaccgctcc tcggcgatcg tcgacgaccc cgacgtaccg gtccgccagg   1020
ggcagccgga cgccgattgg cggcccggca gcgagcccgg gtaccgcgcc gcgcacgcct   1080
ggtgggactc cacgacctcc acgctcgacc tcttcggccg cggcttcgtc ctgctccgct   1140
tcgcggacca cgacggcctc ccggcgatcg agcgcgcgtt cgccgagcgg ggcgtacccc   1200
tgaccgtgca ccaggacac gacacggaga tcgccaagct gtacgcacgc tccttcgtcc   1260
tggtccgccc cgacggtcat gtcgcctggc gcggcgacga cctgcccggc gacccgacgg   1320
ccctggtcga cacggtgcgg ggtgaggccg cgccccgtga accgcggggc tgaggcccac   1380
gcggcctccc gtccgccgat ggggcggctc ggaccgaagc tcctctgacc tgtatgttcc   1440
cacagtccgt gcacggtgcg gaccctgtag ggacgccccg taaactccgt acacgtgact   1500
tctgcgccag ccaagccccg catcccgaac gtcctcgccg gacgctacgc ctccgccgag   1560
ctcgccacgc tctggtcccc cgagcagaag gtgaggctgg agcggcagct ctggctggcc   1620
gtgctgcggg cccagaagga cctcggcatc gaggtgccgg acgaggcgct cgccgactac   1680
gagcgggtcc tcgacaccgt cgacctggcc tccatcgccg agcgcgagaa ggtcacgcgg   1740
cacgacgtga aggcgcggat cgaggagttc aacgacctcg ccgggcacga gcacgtgcac   1800
aagggcatga cctcccggga cctcacggag aacgtcgagc agctg               1845
```

<210> SEQ ID NO 6
<211> LENGTH: 9
<212> TYPE: PRT
<213> ORGANISM: Streptomyces longisporoflavus
<220> FEATURE:
<223> OTHER INFORMATION: methyl-transferase like sequence motif from
      Staurosporin O-MT

<400> SEQUENCE: 6

Val Leu Asp Leu Gly Cys Gly Val Gly
  1               5

<210> SEQ ID NO 7
<211> LENGTH: 9
<212> TYPE: PRT
<213> ORGANISM: Streptomyces sp.
<220> FEATURE:
<223> OTHER INFORMATION: sequence motif from Streptomyces erythraea
      erythromycin O-MT

<400> SEQUENCE: 7

Val Leu Asp Val Gly Phe Gly Leu Gly
  1               5

<210> SEQ ID NO 8
<211> LENGTH: 9
<212> TYPE: PRT
<213> ORGANISM: Streptomyces peucetius
<220> FEATURE:
<223> OTHER INFORMATION: methyl transferase like sequence motif from
      carminomycin O-MT -continued

```
<400> SEQUENCE: 8

Val Leu Asp Val Gly Gly Gly Lys Gly
 1               5

<210> SEQ ID NO 9
<211> LENGTH: 9
<212> TYPE: PRT
<213> ORGANISM: Streptomyces mycarofaciens
<220> FEATURE:
<223> OTHER INFORMATION: methyl transferse like sequence motif from
      midamycin O-MT

<400> SEQUENCE: 9

Val Leu Glu Ile Gly Thr Gly Thr Gly
 1               5

<210> SEQ ID NO 10
<211> LENGTH: 9
<212> TYPE: PRT
<213> ORGANISM: Streptomyces glaucescens
<220> FEATURE:
<223> OTHER INFORMATION: methyl transferase sequence motif from
      tetracenomycin O-MT

<400> SEQUENCE: 10

Phe Val Asp Leu Gly Gly Ala Arg Gly
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:
      consensus O-MT sequence motif

<400> SEQUENCE: 11

Val Leu Asp Ile Gly Gly Gly Thr Gly
 1               5
```